(12) United States Patent
Cheng et al.

(10) Patent No.: US 7,667,835 B2
(45) Date of Patent: Feb. 23, 2010

(54) APPARATUS AND METHOD FOR PREVENTING COPPER PEELING IN ECP

(75) Inventors: Hsi-Kuei Cheng, Jhbei (TW); Jung-Chih Tsao, Tainan (TW); Hsien-Ping Feng, Youghe (TW); Ming-Yuan Cheng, Taipei (TW); Steven Lin, Hsinchu (TW); Ray Chuang, Taipei (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 344 days.

(21) Appl. No.: 11/510,951

(22) Filed: Aug. 28, 2006

(65) Prior Publication Data

US 2008/0047827 A1    Feb. 28, 2008

(51) Int. Cl.
*G01N 21/00* (2006.01)
*G01N 21/55* (2006.01)
*G01B 11/28* (2006.01)
*C25D 21/12* (2006.01)
*H01L 21/00* (2006.01)

(52) U.S. Cl. .................... 356/237.5; 356/445; 356/630; 205/84; 438/7

(58) Field of Classification Search .................. None
See application file for complete search history.

(56) References Cited

U.S. PATENT DOCUMENTS

| | | | | |
|---|---|---|---|---|
| 3,827,963 A * | 8/1974 | Callahan | .................. | 204/228.6 |
| 5,270,222 A * | 12/1993 | Moslehi | .......................... | 438/7 |
| 5,719,495 A * | 2/1998 | Moslehi | .................... | 324/158.1 |
| 6,159,073 A * | 12/2000 | Wiswesser et al. | .............. | 451/6 |
| 6,190,234 B1 * | 2/2001 | Swedek et al. | ................. | 451/6 |
| 6,633,831 B2 * | 10/2003 | Nikoonahad et al. | ......... | 702/155 |
| 6,690,473 B1 * | 2/2004 | Stanke et al. | ................. | 356/601 |
| 6,722,946 B2 * | 4/2004 | Talieh et al. | .................... | 451/8 |
| 6,879,051 B1 * | 4/2005 | Singh et al. | .................. | 257/798 |
| 6,934,040 B1 * | 8/2005 | Schietinger et al. | .......... | 356/630 |
| 7,586,597 B2 * | 9/2009 | Yim et al. | ................. | 356/237.2 |
| 2003/0129774 A1 * | 7/2003 | Christian et al. | ............... | 438/10 |
| 2004/0007325 A1 * | 1/2004 | Pan et al. | .................. | 156/345.1 |
| 2004/0138838 A1 * | 7/2004 | Scheiner et al. | ............... | 702/64 |
| 2005/0018196 A1 * | 1/2005 | Kusuda | ....................... | 356/448 |
| 2005/0245086 A1 * | 11/2005 | Wang et al. | .................. | 438/690 |
| 2006/0266653 A1 * | 11/2006 | Birang et al. | .................. | 205/83 |
| 2007/0003259 A1 * | 1/2007 | Kaihori | ....................... | 392/416 |
| 2007/0052977 A1 * | 3/2007 | Wang | .......................... | 356/630 |
| 2009/0146143 A1 * | 6/2009 | Bolom et al. | .................. | 257/48 |

* cited by examiner

*Primary Examiner*—Tarifur Chowdhury
*Assistant Examiner*—Gordon J Stock, Jr.
(74) *Attorney, Agent, or Firm*—Thomas, Kayden, Horstemeyer & Risley

(57) ABSTRACT

An apparatus and method for preventing the peeling of electroplated metal from a wafer, is disclosed. The apparatus includes a seed layer detector system having a light source and a reflectivity detector. According to the method, the light source emits a beam of light onto a wafer and the reflectivity detector receives the light reflected from the wafer. The reflectivity of the wafer surface is measured to determine the presence or absence of a seed layer on the wafer, as well as whether the seed layer has a minimum thickness for optimum electroplating of a metal onto the seed layer.

15 Claims, 2 Drawing Sheets

APPARATUS AND METHOD FOR PREVENTING COPPER PEELING IN ECP

FIELD OF THE INVENTION

The present invention relates to electrochemical plating (ECP) processes used to deposit metal layers on semiconductor wafer substrates in the fabrication of semiconductor integrated circuits. More particularly, the present invention relates to an apparatus and method for preventing peeling of copper from wafers in an electrochemical plating process by ascertaining the presence of a seed layer on the wafers prior to the ECP process.

BACKGROUND OF THE INVENTION

When a copper layer is deposited on a substrate, such as by electrochemical plating, the copper layer must be deposited on a metal seed layer such as copper which is deposited on the substrate prior to the copper ECP process. As shown in FIG. 1, during an ECP process a contact ring 14 is positioned in close proximity to a wafer 10 as copper is electroplated onto a seed layer 12 which was previously deposited on the wafer 10 prior to the ECP process. The contact ring 14 serves as an electrical conduit between the wafer 10 and an electroplating current source (not shown) and facilitates monitoring of the electrical resistance of the wafer 10 during the ECP process. The electrical resistance of the wafer 10 reveals the presence or absence of the seed layer 12 on the wafer 10.

In the event that the seed layer 12 is insufficiently thin or absent from the wafer 10, copper electroplated onto the wafer 10 has a tendency to peel off of the wafer 10 into the electroplating bath. This contaminates the wafer 10 and subsequent wafers 10 processed in the ECP bath solution. Therefore, the electrical resistance of the wafer 10, as measured through the contact ring 12, serves as a precautionary tool to verify that the seed layer 12 is present on the wafer 10 and of sufficient thickness upon commencement of the ECP process.

However, electrical conductivity of the wafer 10 has been found to be an unreliable indicator as to the thickness characteristics of the seed layer 12 on the wafer 10. Furthermore, seed layer verification can only take place after the wafer 10 is immersed in the electroplating bath solution and electroplating has begun. Therefore, a novel apparatus and method is needed to verify the presence or absence of a seed layer and the thickness of a seed layer on a wafer prior to commencement of an ECP process.

SUMMARY OF THE INVENTION

In accordance with these and other objects and advantages, the present invention is generally directed to an apparatus and method which substantially prevents or eliminates peeling of electroplated copper from a wafer during a copper electrochemical plating (ECP) process by ascertaining the presence or absence of a seed layer on the wafer, as well as whether the seed layer has a minimum thickness for electroplating, prior to the ECP process. The apparatus includes a seed layer detector system having a light source for emitting a beam of light onto a wafer and a reflectivity detector which receives the light reflected from the wafer and measures the reflectivity of the wafer surface to determine the presence or absence of a seed layer on the wafer.

According to a typical method of the invention, a beam of light is reflected from the wafer into a reflectivity detector which measures the reflectivity of the wafer surface. The presence or absence of a seed layer on the wafer surface, as well as whether the seed layer has a sufficient thickness for electrochemical plating of a metal on the seed layer, is revealed by the measured reflectivity. In the event that the seed layer is either absent from the wafer surface or has a thickness which is less than an optimum thickness for electrochemical plating, transfer of the wafer into the ECP apparatus is halted and the wafer is re-routed through the processing sequence to deposit a seed layer on the wafer. In the event that the seed layer is present on the wafer and has the minimum thickness for optimum electrochemical plating, the wafer is transferred into the ECP apparatus for the electrochemical plating of a typically copper layer onto the wafer.

BRIEF DESCRIPTION OF THE DRAWINGS

The invention will now be described, by way of example, with reference to the accompanying drawings, in which.

DETAILED DESCRIPTION OF THE INVENTION

The present invention has particularly beneficial utility in preventing the peeling of an electroplated metal from a wafer due to the absence of a metal seed layer, or the presence of a seed layer having insufficient thickness for optimum electrochemical plating, on the wafer. The invention includes an apparatus and method for preventing the peeling of electroplated metal from a wafer. The apparatus includes a seed layer detector system having a light source which emits a beam of light onto a wafer and a reflectivity detector which receives the light reflected from the wafer and measures the reflectivity of the wafer surface to determine the presence or absence of a seed layer on the wafer, as well as whether the seed layer has a minimum thickness for optimum electroplating of a metal onto the seed layer.

According to a typical method of the invention, a beam of light is reflected from the wafer into a reflectivity detector which measures the reflectivity of the wafer surface. The presence or absence of a seed layer on the wafer surface, as well as whether the seed layer has a sufficient thickness for electrochemical plating of a metal on the seed layer, is revealed by the measured reflectivity. In the event that the seed layer is either absent from the wafer surface or has a thickness which is less than an optimum thickness required for electrochemical plating, transfer of the wafer into the ECP apparatus is halted and the wafer is re-routed through the processing sequence to deposit a seed layer on the wafer. In the event that the seed layer is present on the wafer and has at least the minimum thickness required for optimum electrochemical plating, the wafer is transferred into the ECP apparatus for the electrochemical plating of a typically copper layer onto the wafer.

Figure 1:
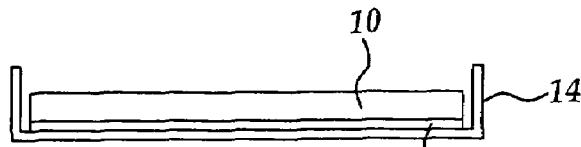
FIG. 1 is a schematic of a contact ring used to conduct current between a wafer and a current source in a conventional electrochemical plating cell.
Figure 2:
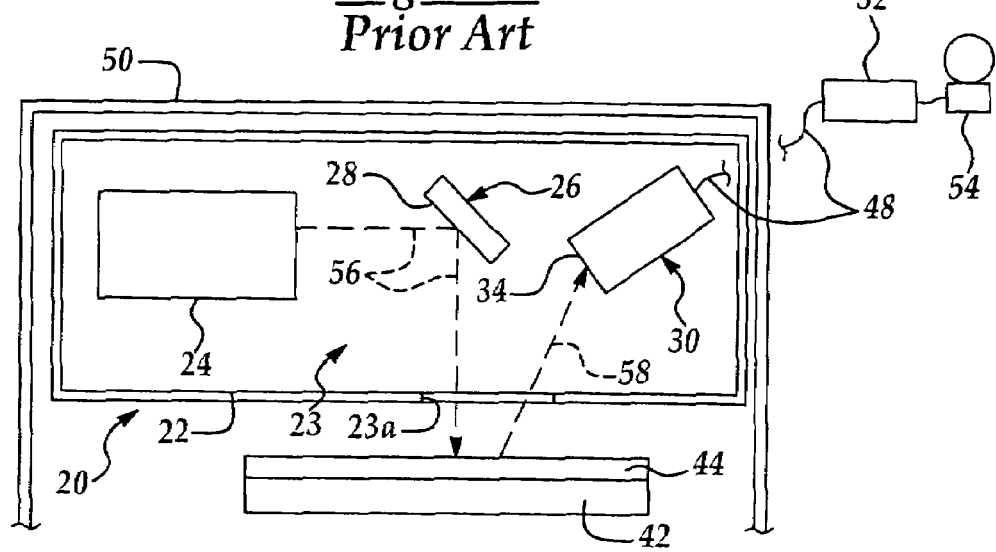
FIG. 2 is a schematic of an illustrative embodiment of the seed layer detector system of the present invention.

Referring to FIG. 2, an illustrative embodiment of the seed layer detector system of the present invention is generally indicated by reference numeral 20. The system 20 is typically provided inside a wafer orientation chamber 50 that is disposed in proximity to an electrochemical plating (ECP) apparatus (not shown) used to electroplate a metal such as copper on wafers. In the wafer orientation chamber 50, which may be conventional, a robot (not shown) aligns a wafer 42 therein for proper positioning of the wafer 42 in the ECP apparatus.

As hereinafter further described, the seed layer detector system 20 is placed typically in the upper portion of the wafer orientation chamber 50. Prior to orientation and transfer of the wafer 42, the system 20 discerns the presence or absence of a seed layer 44 on the wafer 42. In the event that a seed layer 44 is present on the wafer 42, the system 20 determines whether the seed layer 42 has a minimum thickness (typically at least about 100 angstroms) required for electrochemical plating.

As shown in FIG. 2, the seed layer detector system 20 typically includes a system housing 22 having a housing interior 23. The system housing 22 typically includes a bottom housing opening 23a. A lamp 24, which may be any suitable source of visible light, is provided in the housing interior 23. A mirror 26 is further provided in the housing interior 23, above the housing opening 23a, and includes a reflective surface 28 which is disposed at an angle and in spaced-apart relationship with respect to the lamp 24. A reflectivity detector 30 is further provided in the housing interior 23, in spaced-apart relationship to the housing opening 23a, and includes a detector window 34 which is oriented toward the housing opening 23a.

Figure 3:
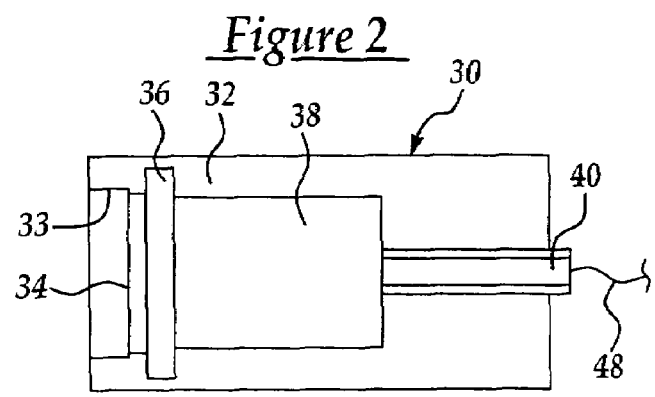
FIG. 3 is a cross-section of a reflectivity detector component of the seed layer detector system of FIG. 2.

As shown in FIG. 3, the reflectivity detector 30 typically includes a detector housing 32 having a front window opening 33. The detector window 34 may be recessed in the window opening 33. An optical filter 36 is provided in the detector housing 32, behind the detector window 34. The optical filter 36 allows light of a specific wavelength to pass from the detector window 34, through the optical filter 36. Preferably, the optical filter 36 allows light having a wavelength of visible light to pass through.

As further shown in FIG. 3, a photo-sensor 38 is provided in the detector housing 32, behind the optical filter 36. The photo-sensor 38 may be conventional and converts light energy to electrical current. A reflectivity gain 40 provided in the detector housing 32 operably engages the photo-sensor 38 to facilitate manual tuning of the reflectivity gain.

As shown in FIG. 2, a microprocessor 52 is operably connected to the reflectivity detector 30, typically using suitable wiring 48. The microprocessor 52 is programmed to calculate a numerical reflectivity value of a typically copper seed layer 44 deposited on the wafer 42, or a numerical reflectivity value of a bare silicon surface, according to the knowledge of those skilled in the art. In typical application, the reflectivity of bare silicon is 1.0. The reflectivity of a copper seed layer 44 having a minimum thickness (at least about 100 angstroms) required for electroplating of a copper layer (not shown) on the seed layer 44 is equal to or larger than 1.3.

An alarm 54, which may be audible, visual or both, is operably connected to the microprocessor 52. During the reflectivity measurement of actual production wafers, in the event that the microprocessor 52 calculates a reflectivity value which is less than 1.3 relative to a reflectivity value larger than 1.3 for a seed layer of minimum thickness, the microprocessor 52 transmits an activation signal to the alarm 54 to activate the alarm 54. The activated alarm 54 notifies personnel as to the absence of a seed layer 44 on the wafer 42 or to the presence of a seed layer 44 having insufficient thickness for optimum electroplating on the wafer 42.

In operation of the seed layer detector system 20, the system 20 is initially calibrated to assign a numerical reflectivity value for bare silicon. Accordingly, a bare silicon wafer 42, without a seed layer 44 thereon, is initially placed in the wafer orientation chamber 50, on a wafer support (not shown) beneath the housing opening 23a of the system housing 22. The lamp 24 emits a visible light beam 56, which is reflected from the reflective surface 28 of the mirror 26; through the housing opening 23a; and onto the bare silicon surface of the wafer 42. The visible light beam 56 is reflected from the wafer 42 enters the reflectivity detector 30 through the detector window 34, as a reflected light beam 58. The photo-sensor 38 converts the reflected light into an electrical current, which is transmitted to the microprocessor 52. Finally, the microprocessor 52 is programmed to assign the resulting electrical current a numerical reflectivity value of 1.0.

After the system 20 is calibrated to assign a numerical reflectivity value for bare silicon, as described herein above, the system 20 is calibrated to assign a numerical reflectivity value for a typically copper seed layer 44 deposited on the wafer 42. Accordingly, a seed layer 44, having a minimum thickness (typically about 100 angstroms) for optimum electrochemical plating of a typically copper layer on the seed layer 44, is initially deposited on a wafer 42. The wafer 42, having the seed layer 44 deposited thereon, is then placed on the wafer support (not shown) in the wafer orientation chamber 50, beneath the housing opening 23a. The process outlined herein above with respect to assigning a reflectivity value for the bare silicon wafer 42 is then carried out to assign a numerical reflectivity value for the seed layer 44 of minimum thickness. Preferably, the numerical reflectivity value assigned for a seed layer 44 having a thickness of 100 angstroms is equal to or greater than 1.3, based on a reflectivity value of 1.0 for bare silicon. The system 20 is thus calibrated for use to determine the presence or absence of a seed layer 44 on actual production wafers 42, as well as whether the seed layer 44 has the minimum thickness for optimum ECP processing.

Figure 4A:
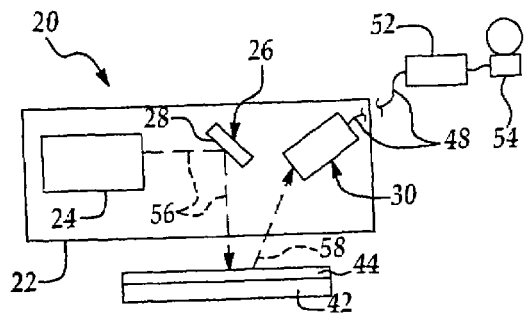
FIG. 4A is a schematic of the seed layer detector system, illustrating reflection of a beam of light from a seed layer on a wafer into the reflectivity detector.
Figure 4B:
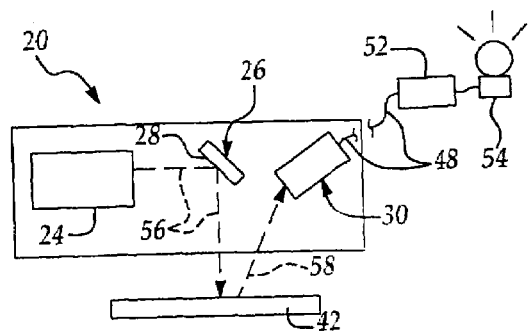
FIG. 4B is a schematic of the seed layer detector system, illustrating reflection of a beam of light from the surface of a wafer which lacks a seed layer, into the reflectivity detector and illumination of a visible alarm.

Referring next to FIGS. 4A and 4B, in conjunction with the flow diagram of FIG. 5, actual production wafers 42 are tested typically as follows. Each production wafer 42 in a wafer lot is individually placed in the wafer orientation chamber 50 (FIG. 2), beneath the housing opening 23a of the system housing 22, as indicated in step 1 of FIG. 5. Next, the reflectivity of the wafer 42, or of the seed layer 44 deposited on the wafer 42, is determined, as indicated in step 2. Accordingly, the lamp 24 emits a visible light beam 56, which is reflected from the reflective surface 28 of the mirror 26; through the housing opening 23a; and onto a seed layer 44 previously deposited on the wafer 42 (FIG. 4A) or onto the wafer 42 (FIG. 4B). The visible light beam 56 is reflected from the seed layer 44 or wafer 42 and enters the reflectivity detector 30, through the detector window 34, as a reflected light beam 58. The photo-sensor 38 (FIG. 3) of the reflectivity detector 30 converts the reflected light beam 58 into an electrical current, which is transmitted to the microprocessor 52.

Figure 5:
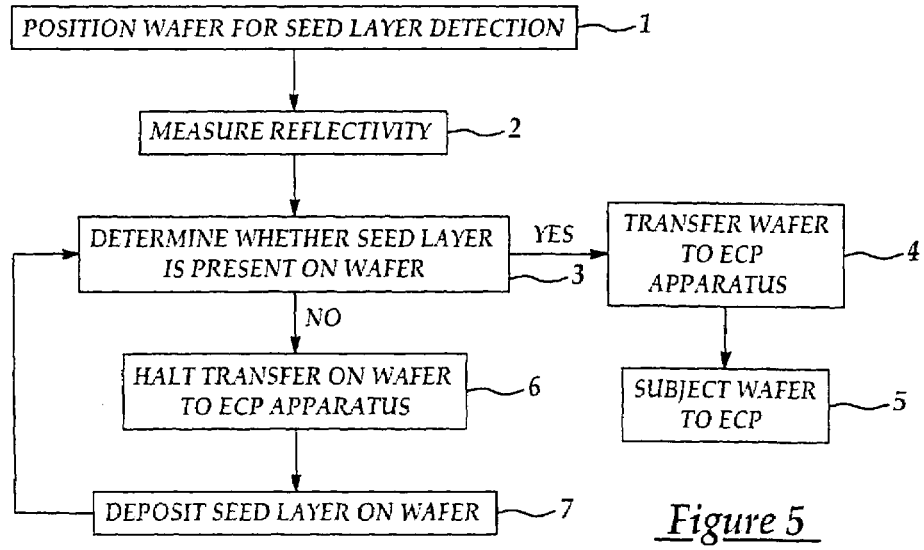
FIG. 5 is a flow diagram illustrating a typical sequential flow of process steps in implementation of the method of the present invention.

As shown in FIGS. 4A and 4B, and indicated in step 3 of FIG. 5, the microprocessor 52 next determines whether or not the seed layer 44 is present on the wafer 42. In the event that the seed layer 44 is present on the wafer 42, the microprocessor 52 further determines whether the seed layer 44 has the minimum thickness required for optimum electroplating of a metal layer such as copper on the seed layer 44 in a subsequent electrochemical plating process. Accordingly, the electrical current received by the microprocessor 52 from the reflectivity detector 30 is converted by the microprocessor 52 into a numerical reflectivity value relative to a reflectivity value of typically 1.0 for bare silicon and a reflectivity value of typically equal to or greater than 1.3 for a seed layer of minimum thickness required for electrochemical plating. The reflectivity value is constant at seed layer thicknesses above 1,000 angstroms.

As shown in FIG. 4A, in the event that the calculated reflectivity value equals or is greater than the predetermined reflectivity value (typically equal to or greater than 1.3) for the seed layer, this indicates both that the seed layer 44 is present on the wafer 42 and the seed layer 44 has the minimum thickness required for ECP processing. Accordingly, the microprocessor 52 does not transmit an electronic signal to the alarm 54. The wafer 42 is then oriented and then transferred from the wafer orientation chamber 50 to the ECP apparatus (not shown), as indicated in step 4 of FIG. 5, for electroplating of a metal layer (not shown) onto the seed layer 44, as shown in step 5.

As shown in FIG. 4B, in the event that the reflectivity value calculated by the microprocessor 52 falls below the predetermined reflectivity value for the seed layer, such as equal to or smaller than 1.3, this indicates that the seed layer 44 is either absent from the wafer 42 or has a thickness which is less than the minimum thickness (typically about 100 angstroms) required for optimum ECP processing. Accordingly, the microprocessor 52 transmits an electrical activation signal to the alarm 54. The alarm 54 is activated to broadcast a visual, audible or both visual and audible signals to personnel to alert the personnel to the absence of a seed layer 44 or to the presence of a seed layer 44 having a thickness which is less than a minimum thickness required for optimum electroplating.

Furthermore, transfer of the wafer 42 from the wafer orientation chamber 50 is halted, as shown in step 6, and the wafer 42 is re-routed through semiconductor processing to deposit the seed layer 44 on the wafer 42, as shown in step 7. The wafer 42 is again tested at step 3, transferred to the ECP apparatus (step 4) and subjected to ECP processing (step 5) in the event that the seed layer 44 is both present on the wafer 42 and of sufficient thickness for optimum ECP processing.

It will be understood by those skilled in the art that the seed layer detector system 20 can be installed in a PVD (physical vapor deposition) chamber (not shown), in which case the seed layer detection process can be carried out immediately after formation of the seed layer 44 on the wafer 42. Alternatively, the seed layer detector system 20 can be used as a single module which is separate from a PVD chamber or ECP apparatus and is used to carry out the seed layer detection process between deposition of the seed layer 44 and electrochemical plating of a metal layer (not shown) on the seed layer 44. Still further in the alternative, and preferably, the wafer orientation chamber 50 shown in FIG. 2 may be an electrochemical plating chamber of an electrochemical plating (ECP) apparatus, in which case the seed layer detector system 20 is incorporated into the electrochemical plating chamber. This enables the seed layer detection process to be carried out immediately prior to formation of metal lines (not shown) on the seed layer 44.

In another embodiment, the method of the invention includes a method of forming metal. The method includes providing a dielectric layer over a substrate, forming an opening in the dielectric layer, forming a metal layer in the opening, measuring a reflectivity of the metal layer and comparing the measured reflectivity with a predetermined reflectivity. The reflectivity of the metal layer is determined in the same manner as was heretofore described with respect to the seed layer 44 of FIGS. 4A, 4B and 5.

While the preferred embodiments of the invention have been described above, it will be recognized and understood that various modifications can be made in the invention and the appended claims are intended to cover all such modifications which may fall within the spirit and scope of the invention.

What is claimed is:

1. A seed layer detector system for a wafer, comprising:
a light source that emits a beam of light against the wafer;
a reflectivity detector disposed in proximity to said light source that receives the beam of light reflected from the wafer and that converts the light into an electrical current;
a microprocessor operably connected to said reflectivity detector that receives the electrical current and that converts the electrical current into a numerical reflectivity value; and
an alarm operably connected to said microprocessor that is activated by said microprocessor when said numerical reflectivity value is less than a predetermined numerical reflectivity value corresponding to a seed layer having a minimum thickness required for electroplating processing.

2. The system of claim 1 further comprising a mirror provided in proximity to said light source that receives the beam of light from said light source and that reflects the beam of light against the wafer.

3. The system of claim 1 further comprising a system housing enclosing said light source and said reflectivity detector.

4. The system of claim 1 wherein said reflectivity detector comprises a detector housing, a detector window provided in said detector housing, an optical filter provided in said detector housing adjacent to said window and a photo-sensor provided in said detector housing adjacent to said optical filter.

5. The system of claim 3 further comprising a mirror provided in proximity to said light source that receives the beam of light from said light source and that reflects the beam of light against the wafer.

6. The system of claim 4 further comprising a mirror provided in proximity to said light source that receives the beam of light from said light source and that reflects the beam of light against the wafer.

7. The system of claim 4 further comprising a system housing enclosing said light source and said reflectivity detector.

8. The system of claim 7 further comprising a mirror provided in proximity to said light source that receives the beam of light from said light source and that reflects the beam of light against the wafer.

9. An apparatus comprising:
a wafer orientation chamber; and
a seed layer detector system for a wafer provided in said chamber, said seed layer detector system comprises a light source that emits a beam of light against the wafer; a reflectivity detector disposed in proximity to said light source that receives the beam of light reflected from the wafer and that converts the light into an electrical current; a microprocessor operably connected to said reflectivity detector that receives the electrical current and that converts the electrical current into a numerical reflectivity value; and an alarm operably connected to said microprocessor that is activated by said microprocessor when said numerical reflectivity value is less than a predetermined numerical reflectivity value corresponding to a seed layer having a minimum thickness required for electroplating processing.

10. The apparatus of claim 9 further comprising a mirror provided in proximity to said light source that receives the beam of light from said light source and reflecting the beam of light against the wafer.

11. The apparatus of claim 9 further comprising a system housing enclosing said light source and said reflectivity detector and wherein said reflectivity detector comprises a detector housing, a detector window provided in said detector housing, an optical filter provided in said detector housing adjacent to said window and a photo-sensor provided in said detector housing adjacent to said optical filter.

12. A method for confirming a presence of a seed layer on a production wafer, comprising the steps of:

providing a production wafer having a top surface;

forming a seed layer on said top surface of the production wafer;

providing a reference numerical reflectivity value obtained on a production wafer having a known seed layer on top or obtained on a bare silicon wafer;

measuring a numerical reflectivity value of said top surface of the production wafer;

determining a presence of said seed layer on the production wafer by comparing said reference numerical reflectivity value to said measured numerical reflectivity value for the production wafer; and providing an alarm and activating said alarm when said numerical reflectivity value for the production wafer is less than a predetermined numerical reflectivity value, and electroplating a metal layer onto the production wafer when said numerical reflectivity value for the production wafer is not less than said predetermined numerical reflectivity value.

13. The method of claim 12 wherein said numerical reflectivity value obtained on the production wafer having the known seed layer on top is 1.3.

14. The method of claim 13, wherein said predetermined numerical reflectivity value is 1.3.

15. The method of claim 13 further comprising the step of subjecting the production wafer to electrochemical plating when said predetermined numerical reflectivity value for the production wafer is at least 1.3.

* * * * *